US009951189B2

United States Patent
Kajitani et al.

(10) Patent No.: US 9,951,189 B2
(45) Date of Patent: Apr. 24, 2018

(54) METHOD FOR MANUFACTURING LIGNIN DEGRADATION PRODUCT

(71) Applicants: Idemitsu Kosan Co., Ltd., Chiyoda-ku, Tokyo (JP); National University Corporation Hokkaido University, Sapporo-shi, Hokkaido (JP)

(72) Inventors: Satoshi Kajitani, Ichihara (JP); Naonori Ryumon, Ichihara (JP); Yoshihito Koyama, Ichihara (JP); Takao Masuda, Sapporo (JP); Teruoki Tago, Sapporo (JP)

(73) Assignees: IDEMITSU KOSAN CO., LTD., Tokyo (JP); NATIONAL UNIVERSITY CORPORATION HOKKAIDO UNIVERSITY, Sapporo-Shi, Hokkaido (JP)

( * ) Notice: Subject to any disclaimer, the term of this patent is extended or adjusted under 35 U.S.C. 154(b) by 0 days.

(21) Appl. No.: 14/776,718

(22) PCT Filed: Mar. 13, 2014

(86) PCT No.: PCT/JP2014/056808
§ 371 (c)(1),
(2) Date: Jan. 6, 2016

(87) PCT Pub. No.: WO2014/142289
PCT Pub. Date: Sep. 18, 2014

(65) Prior Publication Data
US 2016/0145398 A1 May 26, 2016

(30) Foreign Application Priority Data
Mar. 15, 2013 (JP) .................................. 2013-054268

(51) Int. Cl.
*C08H 7/00* (2011.01)
*C07G 1/00* (2011.01)
*C07D 307/46* (2006.01)
(Continued)

(52) U.S. Cl.
CPC ............. *C08H 6/00* (2013.01); *C07D 307/46* (2013.01); *C07D 307/50* (2013.01); *C07G 1/00* (2013.01); *C08H 8/00* (2013.01); *B09B 3/0016* (2013.01)

(58) Field of Classification Search
CPC ... C08H 6/00; C08H 8/00; C07G 1/00; C07D 307/46; C07D 307/50; D21C 3/20
See application file for complete search history.

(56) References Cited

U.S. PATENT DOCUMENTS 2,037,001 A * 4/1936 Aronovsky ............... D21C 3/20
106/123.13
2,166,540 A * 7/1939 Bailey ...................... D21C 3/20
162/37
5,730,837 A * 3/1998 Black ....................... D21C 3/20
127/37

FOREIGN PATENT DOCUMENTS

JP    H-01-258706 A    10/1989
JP    H-06-511043 A    12/1994
(Continued)

OTHER PUBLICATIONS

International Search Report dated Apr. 22, 2014 in PCT/JP2014/056808.

*Primary Examiner* — Nicholas E Hill
(74) *Attorney, Agent, or Firm* — Foley & Lardner LLP (57) ABSTRACT

Provided is a method for producing a lignin degradation product that includes (1) a degradation step of degrading a raw material containing a plant biomass, in a mixed solvent of water and an aliphatic alcohol having from 4 to 10 carbon atoms, which separates into two phases at 0° C. or higher (Continued)

and 50° C. or lower, under the following conditions, and (2) after the degradation step, a liquid-liquid separation step of separating the lignin degradation product-containing organic phase from the solvent that has separated at the temperature for two-phase separation. The method produces a lignin degradation product at a high yield from lignin or a material containing lignin. Condition A: The concentration of the raw material to be in the mixed solvent is 1% by mass or more and 20% by mass or less. Condition B: The reaction temperature is 100° C. or higher and 350° C. or lower. Condition C: The reaction time is 0.1 hours or more and 10 hours or less.

4 Claims, 1 Drawing Sheet

(51) Int. Cl.
*C07D 307/50* (2006.01)
*C08H 8/00* (2010.01)
*B09B 3/00* (2006.01)

(56) References Cited

FOREIGN PATENT DOCUMENTS

| JP | 2010-131013 A | 6/2010 |
| JP | 2012-102297 A | 5/2012 |
| JP | 2012-201645 A | 10/2012 |
| JP | 2012-201828 A | 10/2012 |
| WO | WO-92/13849 A1 | 8/1992 |
| WO | WO-2013/094398 A1 | 6/2013 |

\* cited by examiner

METHOD FOR MANUFACTURING LIGNIN DEGRADATION PRODUCT

TECHNICAL FIELD

The present invention relates to a method for producing a lignin degradation product to be obtained by degrading lignin or by degrading lignin in a lignin-containing material.

BACKGROUND ART

With the increase in environmental problems, bioethanol produced using a carbon-neutral biomass has become noticed as a novel fuel. Heretofore, bioethanol has been produced mainly from raw materials that compete with foods such as starch, sugar, etc., and therefore the problem thereof that would result in the decrease in raw material supply for foods and in the increase in the cost of the material has been pointed out. Given the situation, at present, a technique for producing ethanol from a cellulosic biomass not competing with foods has come to attract rising attention.

The cellulosic biomass includes, for example, trunks and empty fruit bunches of palm, fibers and seeds of palm fruits, bagasse, rice straws, wheat straws, corn residues (corn stovers, corn combs, corn hulls), Jatropha seed coats and hulls, wood chips, switchgrass, Erianthus, energy crops, etc. These all contain cellulose and hemicellulose that can be converted into sugar, and lignin.

Lignin is contained in the solid residue that is separated from cellulose and hemicellulose in the stage where the above-mentioned raw material is saccharified/fermented in the production process for bioethanol. The residue may be utilized as fuel as it is. However, lignin degradation provides phenol derivatives, and therefore rather than using the residue as fuel, developing it into any other chemical industrial products could provide further higher added value.

Consequently, it is desired to develop a method for efficiently producing a lignin degradation product capable of being used as a raw material for the above-mentioned chemical industrial products.

Technology of lignin dissolution has been developed mainly in pulp production. For example, in a kraft pulp method, a chemical agent containing mainly sodium hydroxide (NaOH) and sodium sulfide ($Na_2S$) is added and boiled at 150 to 160° C. or so. On the other hand, in a sulfide pulp method, a mixed liquid of an acidic sulfite salt and sulfurous acid is added and boiled at 130 to 145° to dissolve lignin in wood as a lignin sulfonate salt (for example, see PTL 1).

However, these methods each use a strong alkali or a strong acid, and therefore as the material for the reactor and the fixings to be used therein, alkali-resistant or acid-resistant ones must be selected and the handleability thereof is not good. For example, PTL 1 describes "problems of relatively high equipment cost and contamination" in paragraph [0002]. In addition, the sulfide pulp method produces sulfonated lignin and is therefore limited in point of the use thereof.

Claim 1 in PTL 1 discloses a pulping step where a known pulp raw material such as a woody material or a crop waste, and an aqueous solvent containing from 50 to 90% of a high-boiling-point organic solvent that has a boiling point of from 150 to 250° C. and is at least soluble in water, are filled in a pressure-tight reactor in a liquid ratio of from 4 to 10, and processed therein at a temperature of from 180 to 230° C. In addition, in paragraph [0007], there are mentioned cyclic ethers and polyalcohols as the high-boiling-point solvent. Further, PTL 1 describes the advantage of recycling the high-boiling-point solvent as it is without separating from water. However, the high-boiling-point solvent is expensive and there still remains room for development in point of the degree of solubility in the solvent of the produced lignin.

Also proposed is a method for lignin separation by using an aqueous solvent that contains an organic solvent such as acetic acid, an alcohol solvent or the like, adding sodium hydroxide or a mineral acid as a catalyst, and so on (for example, see PTL 2, [0022]).

As in the above-mentioned PTL 1 and 2, methods for production of a lignin degradation product have been proposed, but from the viewpoint of obtaining a lignin degradation product as a raw material for high-value-added products in the field of chemical industry, from a carbon-neutral biomass in consideration of environmental problems, it is still desired to efficiently produce a lignin degradation product in an energy-saving manner. From this viewpoint, there is still room for improvement in the production methods for a lignin degradation product in the above-mentioned PTLs 1 and 2.

Also proposed is a method for producing a lignin degradation product from a lignocellulose biomass, using a mixed solvent prepared by adding from 5 to 20% by volume of water to an aliphatic alcohol having from 1 to 8 carbon atoms, under the supercritical or subcritical condition for the mixed solvent (see PTL 3).

However, in PTL 3, methanol that is actually used as the aliphatic alcohol in the mixed solvent does not separate under room temperature and the solvent is in a one-phase state. When the mixed solvent is in a one-phase state, the entire amount of the mixed solvent must be distilled for separating the lignin degradation product through distillation, and therefore a large amount of heat energy is consumed.

On the other hand, for example, in a case of a mixed solvent with an alcohol having a lower boiling point than that of water, the alcohol alone may be evaporated away from the mixed solvent and the lignin having dissolved in the alcohol could be precipitated and recovered. However, a part of lignin having dissolved in water could not be recovered. Consequently, according to the method disclosed in PTL 3, the heat energy loss is great and it is difficult to increase the recovery rate of lignin. In addition, the purity of the resultant lignin is low. Further, the production method in PTL 3 requires high-temperature and high-pressure production conditions, and therefore it is considered that the method would require expensive facilities and severe safety measures. In this way, also for the method in PTL 3, further improvement is desired for efficiently producing lignin in an energy-saving manner.

Also proposed is a method for obtaining a lignin degradation product by processing a lignocellulose biomass in a supercritical or subcritical 1-octanol (see PTL 4).

In the method described in PTL 4, a biomass raw material is extracted using a solution of an alcohol alone. The degradation rate of the lignin degradation product in a solution of an alcohol alone is not sufficient. In addition, it is difficult to separate the lignin having dissolved in the alcohol from cellulose and hemicellulose degradation products, and therefore it is difficult to increase the recovery rate of the lignin degradation product and the purity thereof. Further, for efficiently extracting the lignin degradation product, a large amount of an expensive alcohol must be used. In that manner, even in the method in PTL 4, further improvement is desired for efficiently producing a lignin degradation product in an energy-saving manner.

Also proposed is a method for recovering lignin from a lignocellulose substance by pulping with an alcohol having from 1 to 4 carbon atoms, water and NaOH at a temperature lower than 100° C. (see PTL 5, Claim 1). Claim 2 in PTL 5 describes the ratio of water/alcohol of from 10/90 to 90/10.

However, the method described in PTL 5 has the following problems. Specifically, the method requires a neutralization step for recovering lignin; the base recovery in the method is complicated and when the base could not be recovered, the production cost increases; lignin is often contaminated with base-derived impurities, and owing to the impurities, the lignin is denatured and the quality thereof lowers; and the method requires base-resistant reaction facilities.

Also disclosed is a method of bringing a biomass raw material into contact with a mixture of a water-immiscible organic solvent, an acid and a metal salt catalyst dissolved in an acidic aqueous solution, at a predetermined temperature and a predetermined pressure to thereby separate lignin and hemicellulose having dissolved in the solvent and the aqueous phase from each other, and to leave a pure cellulose as such (see PTL 6). Further, PTL 6 describes use of a higher alcohol as the solvent, saying that butanol and isoamyl alcohol are preferred as the higher alcohol and the ratio of the solvent to the acidic water is from 40/60 to 80/20.

However, the method described in PTL 6 has the following problems. Specifically, the method requires an acid neutralization step; since the catalyst is soluble in water, the catalyst recovery is complicated; the lignin is often contaminated with acid and catalyst-derived impurities, and the lignin is denatured by the impurities and the quality thereof may lower; and the method requires acid-resistant reaction facilities.

CITATION LIST

Patent Literature

PTL 1: JP-A 2001-89986
PTL 2: JP-A 2007-112841
PTL 3: Japanese Patent 4982036
PTL 4: Japanese Patent 4759227
PTL 5: JP-T 2013-541512
PTL 6: JP-T 2010-531639

SUMMARY OF INVENTION

Technical Problem

An object of the present invention is to provide a method for producing a lignin degradation product capable of producing a lignin degradation product from lignin or a material containing lignin, at a high yield.

Solution to Problem

The present inventors have assiduously studied and have found that, when a raw material containing a plant biomass is reacted in a mixed solvent of water and an alcohol capable of separating into two phases under a predetermined condition, then the above-mentioned problems can be solved, and have completed the present invention.

Specifically, the production method for a lignin degradation product of the present invention comprises:

(1) a degradation step of degrading a raw material containing a plant biomass, in a mixed solvent of water and an aliphatic alcohol having from 4 to 10 carbon atoms, which separates into two phases at 0° C. or higher and 50° C. or lower, under the following conditions;

Condition A: the concentration of the raw material to be in the mixed solvent is 1% by mass or more and 20% by mass or less, Condition B: the reaction temperature is 100° C. or higher and 350° C. or lower, and Condition C: the reaction time is 0.1 hours or more and 10 hours or less; and (2) after the degradation step, a liquid-liquid separation step of separating the lignin degradation product-containing organic phase from the solvent that has separated at the temperature for two-phase separation.

Advantageous Effects of Invention

According to the present invention, there is provided a production method for a lignin degradation product capable of producing a lignin degradation product from lignin or a material containing lignin, at a high yield.

DESCRIPTION OF EMBODIMENTS

[Production Method for Lignin Degradation Product]

The production method for a lignin degradation product according to an embodiment of the present invention is a method for producing a lignin degradation product from a lignin-containing raw material in a mixed solvent containing water and an alcohol, under the conditions mentioned below. Here, the lignin degradation product is a compound to be obtained by degrading lignin or degrading lignin contained in a lignin-containing raw material. In this embodiment, as the lignin-containing raw material, used is a plant biomass.

The production method for a lignin degradation product according to this embodiment includes (1) a degradation step of degrading a raw material containing a plant biomass, in a mixed solvent of water and an aliphatic alcohol having from 4 to 10 carbon atoms, which separates into two phases at 0° C. or higher and 50° C. or lower, under the following conditions:

Condition A: the concentration of the raw material in the mixed solvent is 1% by mass or more and 20% by mass or less, Condition B: the reaction temperature is 100° C. or higher and 350° C. or lower, and Condition C: the reaction time is 0.1 hours or more and 10 hours or less, and (2) after the degradation step, a liquid-liquid separation step of separating the lignin degradation product-containing organic phase from the solvent that has separated at the temperature for two-phase separation.

<(1) Degradation Step>

As the lignin-containing material applicable to the production method according to the embodiment of the present invention, usable is a plant biomass. The plant biomass includes a woody biomass and a herbaceous biomass. The woody biomass includes cedar trees, cherry trees, eucalyptus trees, cypress trees, false cypress trees, beech trees, etc. The herbaceous biomass includes bamboo, trunks and empty fruit bunches of palm, fibers and seeds of palm fruits, bagasse, rice straws, wheat straws, corn residues (corn stovers, corn combs, corn hulls), Jatropha seed coats and hulls, switchgrass, Erianthus and waste residues that are discharged in a process of squeezing plant oil such as energy crops or the like. Of those, from the viewpoint of the availability and the compatibility with the production method of the present invention, preferred is a herbaceous biomass, and more preferred is bagasse.

The plant biomass is preferred here as containing lignin in an amount of from 15 to 40% by mass. The plant biomass raw material that is introduced into the production step may be a ground one. The plant biomass raw material may be in any form of blocks, chips or powders.

In the degradation step in the production method shown here as the embodiment, used is a mixed solvent of water and an aliphatic alcohol having from 4 to 10 carbon atoms, and the solvent can separate into two phases at 0° C. or higher and 50° C. or lower. By using the mixed solvent of water and an alcohol of the type, the carboxylic acid formed in lignin degradation reaction may react with the alcohol to form an ester. The formed ester provides an effect of inactivating the carboxylic acid that is highly reactive and is readily polymerizable.

In addition, by using the solvent that separates into two phases at 0° C. or higher and 50° C. or lower, the lignin degradation product formed through the degradation reaction can be extracted in the organic phase, while a part of the cellulose degradation product, a part of the hemicellulose degradation product and the metals contained in the biomass are partitioned into the aqueous phase, or that is, the solvent thus provides liquid-liquid separation. Consequently, the impurities in the lignin can be reduced. In addition, according to the liquid-liquid separation, the yield of the lignin degradation product can be increased. Furthermore, according to the liquid-liquid separation, the amount of heat energy to be consumed away in the step of separating the lignin degradation product and the solvent can be reduced, as compared with that in any other separation method of distillation under heat. Consequently, the solvent is useful from the viewpoint of carbon offset.

The solvent usable in the degradation step may be any solvent capable of separating into two phases at 0° C. or higher and 50° C. or lower. The solvent may be also a solvent that separates into two phases by adding water or an alcohol after the degradation reaction even if the solvent is in one phase before or during the degradation reaction.

In the embodiment of the present invention, the alcohol to be used in the solvent is any and every aliphatic alcohol having from 4 to 10 carbon atoms and capable of separating from water to be in two phases at 0° C. or higher and 50° C. or lower. For example, the alcohol may be a saturated linear alcohol such as 1-butanol, 1-pentanol, 1-hexanol, 1-heptanol, 1-octanol, 1-nonanol, 1-decanol, etc.; and, in addition thereto, may also be an unsaturated linear alcohol. Further, the alcohol may be a branched aliphatic hydrocarbon alcohol. Also the alcohol may be an unsaturated branched alcohol. As the branched alcohol, preferably mentioned is isobutanol. Of those alcohols, from the viewpoint of two-phase separation from water at 0° C. or higher and 50° C. or lower, preferred is one or more selected from 1-butanol, 1-pentanol and 1-hexanol, and more preferred is 1-butanol.

On the other hand, methanol, ethanol and propanol that are aliphatic alcohols having from 1 to 3 carbon atoms are unfavorable because they are miscible with water at 0° C. or more and 50° C. or lower to be in one phase.

Further, when an aliphatic alcohol having from 1 to 3 carbon atoms is used, then the softening point of the solvent soluble fraction in the resultant lignin may increase. Lignin is often used in a state dissolving in a solvent, or is soluble in a solvent, or may be mixed with a resin at a relatively low temperature, and for these reasons, the softening point of lignin is preferably low. In a case where lignin is used as a resin and when the molecular weight of lignin in the case is low, then there may be problems that the strength and the heat resistance of lignin as a material would lower. In other words, lignin soluble in solvent and lignin having a low softening point and having a high molecular weight are desired in the art. Here, the weight-average molecular weight (Mw) of the solvent-soluble fraction in lignin is, as measured according to the measurement method described in the section of Examples to be given hereinunder, 1100 or more, preferably 1200 or more, more preferably 1400 or more, and even more preferably 1500 or more. The upper limit needs not to be defined, but is preferably 5000 or less. The softening point is, as measured according to the measurement method described in the section of Examples to be given hereinunder, 135° C. or lower, preferably 125° C. or lower, more preferably 120° C. or lower. The lower limit needs not to be defined, but is preferably 50° C. or higher.

The concentration of the raw material to be in the solvent under the condition A is from 1% by mass or more and 20% by mass or less, preferably from 3% by mass or more and 18% by mass or less, more preferably 5% by mass or more and 15% by mass or less. When the raw material concentration is less than 1% by mass, then the amount of energy to be used for heating the solvent and for separating the lignin degradation product from the solvent would increase and therefore the energy efficiency in the production process for the lignin degradation product would worsen. When the material concentration is more than 20% by mass, then the solvent amount would not be sufficient and the reaction efficiency would thereby worsen.

The reaction temperature under the condition B is 100° C. or higher and 350° C. or lower, preferably 150° C. or higher and 300° C. or lower, more preferably 170° C. or higher and 270° C. or lower. When the temperature is lower than 100° C., then it is unfavorable since the lignin degradation reaction could hardly go on, but when higher than 350° C., then it is also unfavorable since cellulose would degrade and the lignin degradation product would again polymerize to form coke.

The reaction time under the condition C is 0.1 hours or more and 10 hours or less, preferably 0.2 hours or more and 8 hours or less, more preferably 1 hour or more and 6 hours or less, and even more preferably 1 hour or more and 3 hours or less. When the time is less than 0.1 hours, then the degradation reaction could not fully go on, but when more than 10 hours or more, the amount of coke to be formed by degradation of cellulose and by repolymerization of the lignin degradation product could not be prevented from increasing.

Water to be used along with the solvent in the embodiment of the present invention includes, for example, tap water, industrial water, ion-exchanged water, distilled water, etc. In a case where 1-butanol is used as the aliphatic alcohol, the range of the blend ratio of water and the alcohol is, as a ratio by mol, preferably such that water (mol)/1-butanol (mol) is from 0.5/1 to 45/1, more preferably from 0.7/1 to 30/1, even more preferably from 0.9/1 to 20/1, still more preferably from 1.8/1 to 10/1.

In a case where 1-hexanol is used as the aliphatic alcohol, the molar ratio is preferably such that water (mol)/1-hexanol (mol) is from 0.5/1 to 45/1, more preferably from 0.7/1 to 20/1, even more preferably from 1.5/1 to 10/1.

In a case where 1-octanol is used as the aliphatic alcohol, the molar ratio is preferably such that water (mol)/1-octanol (mol) is from 0.5/1 to 45/1, more preferably from 1/1 to 30/1, even more preferably from 1.8/1 to 20/1.

When the ratio of water to the alcohol is more than the above-mentioned range, then the solvent could not separate into two phases of water and alcohol under the predetermined condition. In addition, in the case, extraction efficiency for the lignin degradation product may lower.

Further, when water is used in an amount more than the above-mentioned preferred range, then the molecular weight of the solvent-soluble fraction in the resultant lignin may lower. Lignin is often used in a state dissolving in a solvent, or is soluble in a solvent, or may be mixed with a resin at a relatively low temperature, and for these reasons, the softening point of lignin is preferably low. However, in a case where lignin is used as a resin and when the molecular weight of lignin in the case is low, then there may be problems that the strength and the heat resistance of lignin as a material would lower. In other words, lignin soluble in solvent and lignin having a low softening point and having a high molecular weight are desired in the art. Here, the weight-average molecular weight (Mw) of the solvent-soluble fraction in lignin is, as measured according to the measurement method described in the section of Examples to be given hereinunder, 1100 or more, preferably 1200 or more, more preferably 1400 or more, and even more preferably 1500 or more. The upper limit needs not to be defined, but is preferably 5000 or less. The softening point is, as measured according to the measurement method described in the section of Examples to be given hereinunder, 135° C. or lower, preferably 125° C. or lower, more preferably 120° C. or lower. The lower limit needs not to be defined, but is preferably 50° C. or higher. On the other hand, use of an increased amount of alcohol here would result in increase in the cost. In other words, producing the product at the preferred ratio of water/alcohol as described above satisfies the balance between the cost and the performance of the resultant lignin.

In addition to the above-mentioned conditions, it is desirable that the pressure of the reaction system in the degradation step is from 0.5 MPa to 30 MPa. More preferred conditions could be suitably defined as depending on the amount of water and alcohol and the temperature. The degradation step may be carried out in air. It is desirable that the degradation step is carried out in an atmosphere where oxygen is reduced through nitrogen purging for the purpose of preventing polymerization by oxidation in the step.

The reaction mode for the lignin degradation reaction in the production method of the embodiment of the present invention is not specifically defined. For example, employable is any ordinary batch reactor or semi-batch reactor. Also employable is a mode of performing the reaction while extruding a slurry containing a lignin-containing material, water and alcohol by a screw, a pump or the like. Further, static reaction is possible here.

<(2) Liquid-Liquid Separation Step>

The production method for a lignin degradation product of the present invention includes (2) a liquid-liquid separation step. The liquid-liquid separation step is carried out after the degradation step. In the liquid-liquid separation step, the organic phase that contains the lignin degradation product is separated from the solvent at the temperature for two-phase separation. The solvent for use in the production method of the present invention may be any one that secures two-phase separation in a temperature range of 0° C. or higher and 50° C. or lower.

According to the production method for a lignin degradation product of this embodiment, the separated organic phase may be separated through a separatory funnel to give the intended lignin degradation product. The lignin degradation product is kept dissolving in the aliphatic alcohol of the organic phase in the mixed solvent.

In that manner, according to the production method for a lignin degradation product of the present invention, the lignin degradation product can be separated from the solvent in a mode of liquid/liquid separation, and therefore the heat energy loss in the separation step can be reduced.

<(3) Other Step>

In the present invention, it is desirable that, after the liquid-liquid separation step, the lignin degradation product (solid) after concentration of the solvent is processed for extraction treatment (extraction step).

The organic solvent usable in the extraction step may be one alone or a mixed solvent of two or more selected from tetrahydrofuran, acetone, methyl ethyl ketone, diethyl ether, ethyl acetate, acetonitrile, N,N-dimethylformamide, dimethyl sulfoxide, alcohol, toluene, benzene and aliphatic alkanes, or a mixed solvent thereof with water.

The usable organic solvent is preferably one alone or a mixed solvent of two or more selected from tetrahydrofuran, acetone, methyl ethyl ketone, dimethyl ether, diethyl ether, ethyl acetate, acetonitrile, N,N-dimethylformamide, dimethyl sulfoxide and alcohol, or a mixed solvent thereof with water. More preferred is one alone or a mixed solvent of two or more selected from acetone, ethyl acetate, dimethyl ether and alcohol, or a mixed solvent thereof with water.

The alcohol includes methanol, ethanol and propanol, and among them, methanol is preferred. The aliphatic alkane includes octane, heptane, hexane, etc., and among them, hexane is preferred.

Between the degradation step where a lignin-containing material is processed under the condition of A, B and C while the blend ratio of water and alcohol is set in a specific ratio, and the liquid-liquid separation step that is a previous step for extracting the organic solvent-soluble fraction, there may be provided any other step for removing impurities or for forming the lignin degradation product. In addition, between the liquid-liquid separation step and the extraction step, there may also be provided any further step.

<Use of Lignin Degradation Product>

The lignin degradation product produced according to the production method of the embodiment of the present invention may be, after separated from the solid fraction through a filter or the like, used as a raw material for various types of resin monomers, various types of resin additives, resin raw materials, adhesives, chemical products, food products, additives in the field of medicines, etc.

From the lignin degradation product, phenolic compounds such as phenol, guaiacol, cresol and the like may be produced. In addition, from the lignin degradation product, aromatic compounds such as benzene, toluene and the like may be produced. The production reaction may be carried out, for example, using an $FeOx\text{-}ZrO_2$ catalyst or an $FeOx\text{-}Al_2O_3\text{---}ZrO_2$ catalyst in the presence of water at a temperature of from 200 to 500° C. or so.

In addition, the lignin degradation product produced according to the production method of this embodiment may be used concretely as a water-repellent material for fuel, cement. In addition to these, the product may also be usable as a base resin raw material for phenol resins and epoxy resins, and for an additive (curing agent) to epoxy resins, etc. The use is based on the characteristic feature of lignin that has a phenolic structural unit.

Here, use for a base resin raw material, any heretofore-known technique may be employed. As one example, there may be mentioned a resin composition containing a lignin degradation product and a known crosslinking agent typified by hexamethylenetetramine.

In the resin composition containing a lignin degradation product and a crosslinking agent, if desired, various types of fillers as well as any ordinary phenolic resin to be produced industrially may be incorporated. The resin composition of the type may be used as heat insulating materials for housing, electronic parts, resins for frac sands, resins for coated sands, resins for immersion, resins for lamination, and resins for FRP molding, as well as reinforcing materials for automobile parts, automobile tires, etc.

By introduction of an epoxy group into the lignin degradation product or by use of the lignin degradation product as an epoxy resin curing agent, the lignin degradation product is thus applicable to epoxy resins. In addition, using known techniques, a vinyl group, a maleimide group, an isocyanate group or the like may be introduced into the lignin degradation product, and thus the lignin degradation product may be applicable to industrial resins in further broader ranges.

According to the production method for a lignin degradation product of the present invention, a lignin degradation product can be efficiently extracted from a biomass raw material under mild conditions. As a result, a part of cellulose degradation products and a part of hemicellulose degradation products contained in a biomass raw material may be dissolved in an aqueous phase and efficiently recovered at high purity. On the other hand, cellulose can be recovered efficiently and at high purity as a solid.

The amount of lignin to be contained in cellulose, hemicellulose and degradation products thereof that may be obtained in the production method for a lignin degradation product of the present invention is small, therefore realizing efficient saccharification thereof with acid or enzyme. In addition, from cellulose, hemicellulose and degradation products thereof that may be obtained in the production method of the present invention, ethanol and butanol may be produced according to known methods.

In addition, from cellulose and hemicellulose in the present invention, obtainable are rubber and tire-reinforcing material as resin-reinforcing fibers/substitutes for chemical fibers such as cellulose nanofibers, etc., food additives such as carboxymethyl cellulose, oligosaccharides, xylitol, etc., as well as chemical products such as lactic acid, succinic acid, furfural, etc., and these are useful.

EXAMPLES

The present invention will be described in more detail below with reference to the following Examples. However, these Examples are not intended to limit the present invention thereto.

The evaluation data added to the original application are for clarifying the difference of the present invention from the patent literature that has been newly found after the application date of the original application. The already-existing data indicate the yield of the entire lignin degradation product (this is nearly equal to the yield of lignin) while, on the other hand, the added evaluation data indicate the yield of the solvent-soluble fraction relative to lignin contained in the raw material and referred to as 100% (the solvent-soluble fraction corresponds to lignin having a weight-average molecular weight (Mw) of from 500 to 2000 in the measurement method described in the section of the following Examples). The value is one obtained in using the "concentrated lignin degradation product" produced in Example 1 and after the extraction step (the calculation method will be described below).

Examples and Comparative Examples

Example 1

Figure 1:
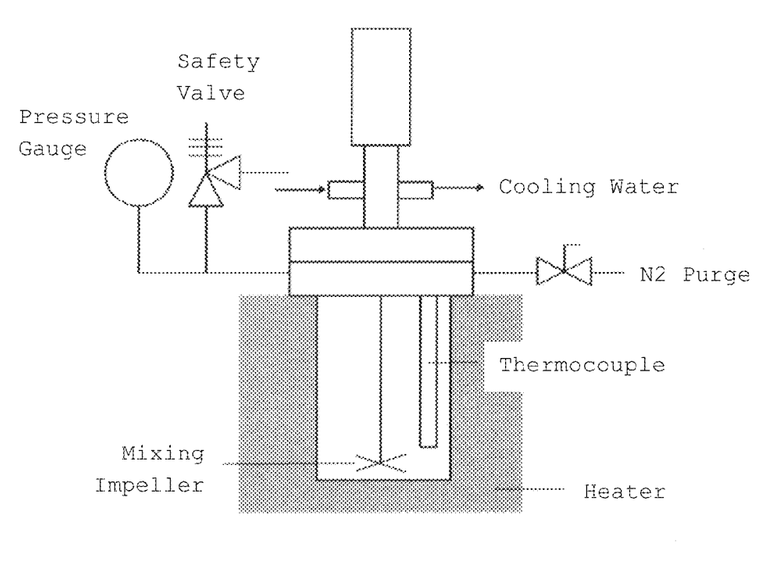
FIG. 1 This is a view showing a batchwise reaction apparatus used in Examples and Comparative Examples.

A plant biomass described Table 1 (sample size, 3 mm or less), and a solvent prepared from an alcohol described in Table 2 in a ratio of water/alcohol also described therein were put in a SUS-made batch reaction apparatus (FIG. 1) having an internal volume of 0.92 L. The total amount of the solvent was 315 g. At the concentration of the starting material and under the degradation reaction condition shown in Table 2, the degradation reaction was carried out.

The reactor of the SUS-made batch reaction apparatus was purged with nitrogen, then heated up to 200° C., and reacted for 2 hours. The reaction time was the lapse time after having reached 200° C. The temperature was measured with a thermocouple.

After the reaction, the reactor of the SUS-made batch reaction apparatus was cooled, and after the temperature lowered to near room temperature, all the contents in the reactor were taken out. After the reaction, the solid fraction and the liquid phase were separated, and the aqueous phase and the organic phase of the filtrate were separated through a separatory funnel. The solid fraction was ultrasonically washed in 200 mL of 1-butanol (the organic solvent used for the reaction) for 15 minutes, and further the solid fraction was ultrasonically washed in 200 mL of acetone for 5 minutes, and then processed for solid-liquid separation, and the resultant filtrate was added to the above organic phase.

The organic phase was evaporated with an evaporator (70° C., water bath), and then dried in vacuum at 125° C. for 1 hour to give a concentrated lignin degradation product. Subsequently, the mass of the concentrated product was measured.

The compound contained in the organic phase before evaporation with the evaporator was identified through gas chromatography, which contained a hemicellulose overdegradation product furfural and a cellulose overdegradation product hydroxymethylfurfural. The concentrated lignin degradation product contained, based on the total mass of the concentrated product, 0.3% hydroxymethylfurfural and 99.7% lignin degradation product.

The resultant concentrated lignin degradation product was put into a beaker containing therein ethyl acetate (67 mL/g—concentrated product), and stirred for 20 minutes. After stirring, this was left statically as it was for 10 minutes, and the supernatant liquid was removed through decantation. The supernatant was filtered under reduced pressure to remove a slight amount of the solid fraction.

Ethyl acetate (33 mL/g—concentrated product) was added to the solid fraction having remained in the beaker, and stirred for 20 minutes. After stirring, this was left statically as such for 10 minutes, and then the supernatant was removed through decantation. The supernatant was filtered under reduced pressure to remove a slight amount of the solid fraction.

Ethyl acetate (13 mL/g—concentrated product) was added to the solid fraction having remained in the beaker, and stirred for 10 minutes. After stirring, this was left statically as such for 10 minutes, the supernatant was again removed through decantation. The supernatant was filtered under reduced pressure to remove a slight amount of the solid fraction.

The resultant supernatant (ethyl acetate-soluble fraction) was evaporated with an evaporator (60° C., water bath), and then dried in vacuum at 150° C. for 30 minutes to give an ethyl acetate-soluble fraction. Subsequently, the mass of the ethyl acetate-soluble fraction was weighed. From the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

Examples 2 to 13

Using a solvent prepared from an alcohol described in Table 2 in a ratio of water/alcohol also described therein and a plant biomass described Table 1, and under the condition shown in Table 2, a lignin degradation product and an ethyl acetate-soluble fraction were produced. In addition, in the same manner as in Example 1, ethyl acetate extraction was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

Example 14

Using a solvent prepared from an alcohol described in Table 2 in a ratio of water/alcohol also described therein and a plant biomass described Table 1, and under the condition shown in Table 2, a lignin degradation product and an ethyl acetate-soluble fraction were produced. After the reaction, the solid fraction and the liquid phase were separated in a mode of solid-liquid separation through filtration. The solid fraction was washed with 200 mL of water, and the resultant wash was added to the previous filtrate. Accordingly, the system separated into two phases of water and 1-butanol, and the 1-butanol phase was recovered through liquid-liquid separation. The solid fraction was ultrasonically washed in 200 mL of 1-butanol for 15 minutes, then processed for solid-liquid separation, and the resultant filtrate was added to the previous 1-butanol phase. The 1-butanol phase was evaporated with an evaporator (70° C., water bath), and then dried in vacuum at 125° C. for 1 hour to give a concentrated lignin degradation product. Subsequently, the mass of the concentrated lignin degradation product was measured. From the amount of the raw material processed here, the lignin content ratio in the raw material shown in Table 1, and the dry mass of the organic phase, the ratio of the lignin degradation product in the organic phase was calculated according to the method mentioned below.

In addition, the same ethyl acetate extraction as in Example 1 was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

Examples 15 to 33

Using a solvent prepared from an alcohol described in Table 3 in a ratio of water/alcohol also described therein and a plant biomass described Table 1, and under the condition shown in Table 3, a lignin degradation product and an ethyl acetate-soluble fraction were produced. In addition, in the same manner as in Example 1, ethyl acetate extraction was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

In addition, the above solvent-soluble fraction was analyzed through gel permeation chromatography (GPC) using a tetrahydrofuran solvent at a measurement temperature of 40° C. and using a RI detector, thereby determining the molecular weight distribution thereof. In addition, the polystyrene-equivalent weight-average molecular weight (Mw) of the fraction was calculated, and the data are shown in Table 5 and Table 6.

Further, the solvent-soluble fraction was put on an aluminium tray, and the aluminium tray was gradually heated on a hot plate to visually measure the softening point of the solvent-soluble fraction. The data are shown in Table 5 and Table 6.

Comparative Examples 1 to 6

The reaction was carried out under the same condition as in Example 1 except that 315 g of water alone was used in place of water and 1-butanol. After the reaction, the lignin degradation product precipitated along with the solid fraction, and therefore the lignin degradation product and the solid fraction and water were separated in a mode of solid-liquid separation through filtration. The resultant solid fraction was recovered, and ultrasonically washed in 200 mL of 1-butanol for 15 minutes to thereby separate the solid fraction from 1-butanol with the lignin degradation product dissolving therein, in a mode of solid-liquid separation. The solvent in the organic phase was evaporated away with an evaporator (70° C., water bath), and then the resultant residue was dried in vacuum at 125° C. for 1 hour to give a concentrated lignin degradation product. Subsequently, the mass was measured. From the amount of the raw material processed here, the lignin content ratio in the raw material shown in Table 1, and the dry mass of the organic phase, the proportion of the lignin degradation product in the organic phase was calculated according to the method described below.

In addition, the same ethyl acetate extraction as in Example 1 was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

Comparative Examples 7 and 8

The reaction was carried out under the same condition as in Example 1 except that existing lignin (dealkalized lignin, available from Tokyo Chemical Industry Co., Ltd.) was used as the raw material, thereby preparing an ethyl acetate-soluble fraction, and the yield of the solvent-soluble fraction (% by mass), based on lignin in the raw material, was calculated.

Comparative Examples 9 to 16

The same reaction as in Examples 16 to 19 was carried out except that an alcohol described in Table 4 was used in place of 1-butanol. After the reaction, the solid fraction and the liquid phase were separated in a mode of solid-liquid separation through filtration. The solid fraction was washed with 200 mL of water, and the resultant wash was added to the previous filtrate. The solid fraction was ultrasonically washed in 200 mL of the organic solvent that had been used in the reaction for 15 minutes, and further the solid fraction was ultrasonically washed in 200 mL of acetone for 5 minutes, and then separated through solid-liquid separation, and the resultant filtrate was added to the previous (filtrate+wash). The organic solvent was evaporated away with an evaporator, and the resultant solid residue was separated through solid-liquid separation by filtration, and then dried in vacuum at 125° C. for 1 hour to give a concentrated lignin degradation product. Subsequently, the mass of the product was measured. From the amount of the raw material processed here, the lignin content ratio in the raw material shown in Table 1, and the dry mass of the organic phase, the ratio of the lignin degradation product in the organic phase was calculated according to the method mentioned below.

In addition, the same ethyl acetate extraction as in Example 1 was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

In addition, the above solvent-soluble fraction was analyzed through gel permeation chromatography (GPC) using a tetrahydrofuran solvent at a measurement temperature of 40° C. and using a RI detector, thereby determining the molecular weight distribution thereof. In addition, the polystyrene-equivalent weight-average molecular weight (Mw) of the fraction was calculated, and the data are shown in Table 5 and Table 6.

Further, the solvent-soluble fraction was put on an aluminium tray, and the aluminium tray was gradually heated on a hot plate to visually measure the softening point of the solvent-soluble fraction. The data are shown in Table 5 and Table 6.

Comparative Example 17

The reaction was carried out under the same condition as in Example 1 except that 315 g of 1-butanol alone was used in place of water and 1-butanol. After the reaction, the solid fraction and the liquid phase were separated in a mode of solid-liquid separation through filtration. The solid fraction was washed with 200 mL of water, and 200 mL of water was added to the resultant wash, and further the resultant liquid was added to the previous filtrate. Accordingly, the aqueous phase and 1-butanol were separated into two phases, and the 1-butanol phase was recovered through liquid-liquid separation. The solid fraction was ultrasonically washed in 200 mL of 1-butanol for 15 minutes, and then processed for solid-liquid separation, and the resultant filtrate was added to the previous 1-butanol phase. The 1-butanol phase was evaporated with an evaporator (70° C., water bath), and then the residue was dried in vacuum at 125° C. for 1 hour to give a concentrated lignin degradation product. Subsequently, the mass of the concentrated lignin degradation product was measured. From the amount of the raw material processed here, the lignin content ratio in the raw material shown in Table 1, and the dry mass of the organic phase, the proportion of the lignin degradation product in the organic phase was calculated according to the method described below.

In addition, the same ethyl acetate extraction as in Example 1 was carried out, and from the amount of the raw material processed here, the lignin content ratio in the raw material shown in Table 1, and the dry mass of the ethyl acetate-soluble fraction, the yield of the solvent-soluble fraction (% by mass), based on lignin in the raw material, was calculated according to the method described below.

[Calculation of Proportion of Lignin Degradation Product in Organic Phase]

The proportion of the lignin degradation product was calculated according to the following equation, based on the lignin content descried in Table 1. Specifically, the equation is as follows.

Proportion of Lignin Degradation Product={(dry mass of organic phase (g))/(amount of raw material (g))/(lignin content ratio in raw material (mass %))×100}×100

[Calculation of Yield of Solvent-Soluble Fraction Based on Lignin in Raw Material]

Based on the lignin content shown in Table 1, the yield was calculated according to the following equation. Specifically, the equation is as follows.

Yield of Solvent-Soluble Fraction based on lignin in raw material={(dry mass of ethyl acetate-soluble fraction (g))/(amount of raw material (g))/(lignin content ratio in raw material (mass %))×100}×100

The component composition in Table 1 was calculated according to pretreatment, measurement of the holocellulose amount, and measurement of the α-cellulose amount, as described below.

<Pretreatment>

As pretreatment, a raw material (cedar, cherry, eucalyptus, bamboo) to be a sample was ground using a Wiley Mill ("MF10" available from IKA Company, sieve size: 1 mm), then dried in an oven at 105° C. for 12 hours, and stored in a desiccator.

<Measurement of Holocellulose Amount (α-Cellulose+Hemicellulose)>

0.5 g of the raw material that had been pretreated in the above was accurately weighed in a 50-mL vial. 20 mL of water, 0.2 g of sodium chlorite and 50 μl of acetic acid were added thereto and mixed, and then heated in a water bath at 70° C. This was heated for 1 hour with stirring at intervals of 20 minutes, and then 0.2 g of sodium chlorite and 50 μl of acetic acid were further added thereto and heated for 1 hour. The operation was repeated until the sample became white. Until the sample became white, 50 μL of acetic acid was added thereto 3 times on average.

The sample was collected on glass fiber filter paper ("GA-100" available from ADVANTEC Co., Ltd.) of which the dry mass had been measured, and washed four to five times with water. Subsequently, this was dried in an oven at 105° C. for 12 hours, and the dry mass of the resultant holocellulose was measured.

<Amount of α-Cellulose>

0.3 g of the holocellulose sample prepared in the manner as above was accurately weighed, and put into a 50-mL vial. 8 mL of an aqueous solution of 17.5% NaOH was added thereto, statically left at 24° C. for 3 minutes, and then the sample was crushed with a glass rod for 5 minutes. After this was left statically at room temperature for 30 minutes, 8 mL of water was added thereto and stirred for 1 minute. After statically left for 5 minutes, the sample was recovered on glass fiber filter paper ("GA-100" available from ADVANTEC Co., Ltd.) of which the dry mass had been measured, then washed two or three times with water, and 10 mL of an aqueous solution of 10% acetic acid was added thereto and filtered. After the filtration, this was further washed 4 or 5 times with water. Subsequently, this was dried in an oven at 105° C. for 12 hours, and the dry mass of the resultant α-cellulose was measured. The value calculated by subtracting the mass of α-cellulose from the holocellulose mass is the mass of hemicellulose.

<Lignin Amount and Constituent Sugar>

In a glass mortar, 0.5 g of the sample was accurately weighed, 16 g of 72% sulfuric acid was added thereto, and the sample was crushed for 1 hour. The contents were transferred into a 500-mL Erlenmeyer flask along with 370 g of distilled water. This was autoclaved (120° C., 60 minutes), then 5 mL of the supernatant was collected, neutralized with 0.1 N NaOH, and subjected to constituent sugar analysis.

The solid fraction was recovered on glass fiber filter paper (GA-100, available from ADVANTEC Co. Ltd.) of which the dry mass had been weighed, and washed 4 or 5 times with water. This was dried in an oven at 105° C. for 12 hours, and then the dry mass thereof was measured. The measured value is the mass of lignin.

TABLE 1

| Component Composition (mass %) | Bagasse | EFB[1] | Cedar | Cherry | Eucalyptus | Bamboo |
|---|---|---|---|---|---|---|
| cellulose | 45.0 | 39.2 | 40.2 | 40.4 | 36.5 | 44.2 |
| hemicellulose | 26.7 | 23.1 | 26.2 | 29.3 | 23.9 | 27 |
| lignin | 25.0 | 26.3 | 33.6 | 30.3 | 39.6 | 28.8 |

In Table 1, EFB is as follows.
[1]EFB: palm empty fruit bunch

TABLE 2

| | | Solvent | | Degradation Condition | | | Proportion of | Yield of | |
|---|---|---|---|---|---|---|---|---|---|
| | Raw Material | Alcohol Used in Solvent | Organic Component in Solvent water/alcohol (mol/mol) | Concentration of Ratio Raw Material raw material/solvent (mass %) | Reaction Temperature (° C.) | Reaction Time (hr) | Lignin Degradation Product in Organic Phase (mass %) | Solvent-Soluble Fraction based on lignin in raw material (mass %) | Yield of Solid Recovery (mass %) |
| Example 1 | cedar | 1-butanol | 8/1 | 2.8 | 200 | 2 | 70.7 | 53.0 | 53.7 |
| Example 2 | cedar | 1-butanol | 8/1 | 5 | 200 | 2 | 67.8 | 50.9 | 53.8 |
| Example 3 | cedar | 1-hexanol | 8/1 | 5 | 200 | 2 | 70.9 | 46.1 | 55.2 |
| Example 4 | cedar | 1-butanol | 8/1 | 2.8 | 220 | 2 | 91 | 68.3 | 42.2 |
| Example 5 | cedar | 1-butanol | 8/1 | 2.8 | 270 | 2 | 100 | 75.0 | 2.6 |
| Example 6 | cherry | 1-butanol | 8/1 | 2.8 | 180 | 2 | 83.4 | 64.2 | 48.1 |
| Example 7 | cherry | 1-butanol | 8/1 | 5 | 200 | 2 | 95.3 | 73.4 | 38.5 |
| Example 8 | cherry | 1-butanol | 8/1 | 2.8 | 200 | 2 | 100 | 77.0 | 40.7 |
| Example 9 | cherry | 1-butanol | 8/1 | 10.9 | 200 | 2 | 87.2 | 67.1 | 45.5 |
| Example 10 | cherry | 1-butanol | 8/1 | 2.8 | 220 | 2 | 100 | 77.0 | 30.9 |
| Example 11 | cherry | 1-butanol | 8/1 | 2.8 | 270 | 2 | 100 | 77.0 | 3.8 |
| Example 12 | eucalyptus | 1-butanol | 8/1 | 5 | 200 | 2 | 70.6 | 53.0 | 48.2 |
| Example 13 | bamboo | 1-butanol | 8/1 | 5 | 200 | 2 | 100 | 88.6 | 32.1 |
| Example 14 | cedar | 1-butanol | 1/1 | 5 | 200 | 2 | 66.7 | 50.0 | 65.8 |

TABLE 3

| | | Solvent | | Degradation Condition | | | Proportion of Lignin | Yield of Solvent-Soluble | |
|---|---|---|---|---|---|---|---|---|---|
| | Raw Material | Alcohol Used in Solvent | Organic Component Ratio in Solvent water/alcohol (mol/mol) | Concentration of Raw Material raw material/solvent (mass %) | Reaction Temperature (° C.) | Reaction Time (hr) | Degradation Product in Organic Phase (mass %) | Fraction based on lignin in raw material (mass %) | Yield of Solid Recovery (mass %) |
| Example 15 | bagasse | 1-butanol | 0.9/1 | 10 | 200 | 2 | 94.2 | 71.3 | 64.6 |
| Example 16 | bagasse | 1-butanol | 2/1 | 10 | 200 | 2 | 100 | 89.3 | 56.7 |
| Example 17 | bagasse | 1-butanol | 4/1 | 10 | 200 | 2 | 100 | 87.5 | 49.4 |
| Example 18 | bagasse | 1-butanol | 8/1 | 10 | 200 | 2 | 97.6 | 77.5 | 50.3 |
| Example 19 | bagasse | 1-butanol | 16/1 | 10 | 200 | 2 | 75.5 | 62.4 | 50.8 |
| Example 20 | bagasse | 1-butanol | 24/1 | 10 | 200 | 2 | 55.4 | 46.8 | 57.3 |
| Example 21 | bagasse | 1-butanol | 40/1 | 10 | 200 | 2 | 42.3 | 38.0 | 56.6 |
| Example 22 | bagasse | i-butanol | 4/1 | 10 | 200 | 2 | 100 | 79.2 | 51.7 |
| Example 23 | bagasse | 1-hexanol | 4/1 | 10 | 200 | 2 | 100 | 80.7 | 48.6 |
| Example 24 | bagasse | 1-hexanol | 8/1 | 10 | 200 | 2 | 100 | 65.6 | 48.3 |
| Example 25 | bagasse | 1-hexanol | 16/1 | 10 | 200 | 2 | 97.1 | 53.1 | 41.7 |
| Example 26 | bagasse | 1-octanol | 4/1 | 10 | 200 | 2 | 95.1 | 72.6 | 50.7 |
| Example 27 | bagasse | 1-octanol | 8/1 | 10 | 200 | 2 | 82.4 | 59.1 | 50.8 |
| Example 28 | bagasse | 1-octanol | 16/1 | 10 | 200 | 2 | 88.8 | 63.2 | 52.2 |
| Example 29 | EFB | 1-butanol | 8/1 | 5 | 200 | 2 | 100 | 90.0 | 28.8 |
| Example 30 | bagasse | 1-butanol | 8/1 | 10 | 210 | 2 | 100 | 86.5 | 45.7 |
| Example 31 | bagasse | 1-butanol | 8/1 | 10 | 220 | 2 | 100 | 98.4 | 35.3 |
| Example 32 | bagasse | 1-butanol | 8/1 | 10 | 200 | 4 | 100 | 82.1 | 47.7 |
| Example 33 | bagasse | 1-butanol | 8/1 | 10 | 200 | 6 | 100 | 92.8 | 46.0 |

TABLE 4

| | Raw Material | Solvent Alcohol Used in Solvent | Solvent Organic Component in Solvent water/alcohol (mol/mol) | Degradation Condition Concentration of Ratio Raw Material raw material/solvent (mass %) | Degradation Condition Reaction Temperature (° C.) | Degradation Condition Reaction Time (hr) | Proportion of Lignin Degradation Product in Organic Phase (mass %) | Yield of Solvent-Soluble Fraction based on lignin in raw material (mass %) | Yield of Solid Recovery (mass %) |
|---|---|---|---|---|---|---|---|---|---|
| Comparative Example 1 | cedar | — | — | 2.8 | 270 | 2 | 37.1 | 37.1 | 27.0 |
| Comparative Example 2 | cedar | — | — | 2.8 | 220 | 2 | 41.5 | 37.4 | 52.9 |
| Comparative Example 3 | cedar | — | — | 2.8 | 200 | 2 | 13.6 | 12.9 | 66.9 |
| Comparative Example 4 | cherry | — | — | 2.8 | 270 | 2 | 42 | 42.0 | 28.0 |
| Comparative Example 5 | cherry | — | — | 2.8 | 220 | 2 | 21.4 | 19.7 | 46.3 |
| Comparative Example 6 | cherry | — | — | 2.8 | 200 | 2 | 15.2 | 14.4 | 58.0 |
| Comparative Example 7 | lignin[2)] | 1-butanol | 8/1 | 2.8 | 200 | 2 | — | 15.6 | — |
| Comparative Example 8 | lignin[2)] | 1-butanol | 8/1 | 3.3 | 250 | 2 | — | 37.8 | — |
| Comparative Example 9 | bagasse | methanol | 0.3/1 | 10 | 200 | 2 | 69.7 | 43.3 | 78.5 |
| Comparative Example 10 | bagasse | methanol | 4/1 | 10 | 200 | 2 | 56.2 | 51.4 | 53.5 |
| Comparative Example 11 | bagasse | ethanol | 2/1 | 10 | 200 | 2 | 69.7 | 50.9 | 59.2 |
| Comparative Example 12 | bagasse | ethanol | 4/1 | 10 | 200 | 2 | 73.8 | 56.1 | 54.9 |
| Comparative Example 13 | bagasse | ethanol | 8/1 | 10 | 200 | 2 | 64.8 | 49.8 | 53.9 |
| Comparative Example 14 | bagasse | ethanol | 16/1 | 10 | 200 | 2 | 50.7 | 43.0 | 58.3 |
| Comparative Example 15 | bagasse | isopropanol | 4/1 | 10 | 200 | 2 | 79.3 | 55.2 | 55.7 |
| Comparative Example 16 | bagasse | acetone | 4/1 | 10 | 200 | 2 | 93.5 | 53.4 | 54.3 |
| Comparative Example 17 | cedar | 1-butanol | 0 | 2.8 | 200 | 2 | 33.6 | 30.9 | 83.5 |

TABLE 5

| | Raw Material | Solvent Alcohol Used in Solvent | Solvent Organic Component Ratio in Solvent water/alcohol (mol/mol) | Degradation Condition Concentration of Raw Material raw material/solvent (mass %) | Degradation Condition Reaction Temperature (° C.) | Degradation Condition Reaction Time (hr) | Weight-Average Molecular Weight of Solvent-Soluble Fraction Mw (g/mol) | Softening Point of Solvent-Soluble Fraction (° C.) |
|---|---|---|---|---|---|---|---|---|
| Example 15 | bagasse | 1-butanol | 0.9/1 | 10 | 200 | 2 | 1473 | 100 |
| Example 16 | bagasse | 1-butanol | 2/1 | 10 | 200 | 2 | 1535 | 115 |
| Example 17 | bagasse | 1-butanol | 4/1 | 10 | 200 | 2 | 1282 | 105 |
| Example 18 | bagasse | 1-butanol | 8/1 | 10 | 200 | 2 | 1245 | 115 |
| Example 19 | bagasse | 1-butanol | 16/1 | 10 | 200 | 2 | 1189 | 125 |
| Example 20 | bagasse | 1-butanol | 24/1 | 10 | 200 | 2 | 1049 | 125 |
| Example 21 | bagasse | 1-butanol | 40/1 | 10 | 200 | 2 | 944 | 125 |
| Example 23 | bagasse | 1-hexanol | 4/1 | 10 | 200 | 2 | 1630 | 125 |
| Example 24 | bagasse | 1-hexanol | 8/1 | 10 | 200 | 2 | 1570 | 120 |
| Example 25 | bagasse | 1-hexanol | 16/1 | 10 | 200 | 2 | 1453 | 125 |
| Comparative Example 11 | bagasse | ethanol | 2/1 | 10 | 200 | 2 | 1396 | 135 |
| Comparative Example 12 | bagasse | ethanol | 4/1 | 10 | 200 | 2 | 1366 | >150 |
| Comparative Example 13 | bagasse | ethanol | 8/1 | 10 | 200 | 2 | 1217 | >150 |
| Comparative Example 14 | bagasse | ethanol | 16/1 | 10 | 200 | 2 | 1109 | 150 |

TABLE 6

| | Raw Material | Solvent | | Degradation Condition | | | Weight-Average | |
|---|---|---|---|---|---|---|---|---|
| | | Alcohol Used in Solvent | Organic Component Ratio in Solvent water/alcohol (mol/mol) | Concentration of Raw Material raw material/solvent (mass %) | Reaction Temperature (° C.) | Reaction Time (hr) | Molecular Weight of Solvent-Soluble Fraction Mw (g/mol) | Softening Point of Solvent-Soluble Fraction (° C.) |
| Example 17 | bagasse | 1-butanol | 4/1 | 10 | 200 | 2 | 1282 | 105 |
| Example 22 | bagasse | i-butanol | 4/1 | 10 | 200 | 2 | 1294 | 110 |
| Example 23 | bagasse | 1-hexanol | 4/1 | 10 | 200 | 2 | 1630 | 125 |
| Example 26 | bagasse | 1-octanol | 4/1 | 10 | 200 | 2 | 1847 | 125 |
| Comparative Example 10 | bagasse | methanol | 4/1 | 10 | 200 | 2 | 1233 | 145 |
| Comparative Example 12 | bagasse | ethanol | 4/1 | 10 | 200 | 2 | 1366 | >150 |
| Comparative Example 15 | bagasse | isopropanol | 4/1 | 10 | 200 | 2 | 1412 | 140 |
| Comparative Example 16 | bagasse | acetone | 4/1 | 10 | 200 | 2 | 1250 | 130 |

In Table 4, lignin is as described below.
2) Lignin: dealkalized lignin, available from Tokyo Chemical Industry Co., Ltd.

Table 2 and Table 3 confirm that, according to the method of separating a lignin degradation product using a solvent that separates into two phases, as in Examples 1 to 13 and Examples 15 to 33, and according to the method of separating a lignin degradation product through two-phase separation after addition of water prior to the degradation step where the system is in one phase, as in Example 14, a lignin degradation product and a solvent-soluble fraction can be obtained at a high yield, as compared with the method of extracting a lignin degradation product from water alone, from an organic solvent alone or from a one-phase mixed solvent as in Comparative Examples 1 to 6 and Comparative Examples 11 to 16.

In addition, it is known that the method of producing a lignin degradation product from a woody or herbaceous raw material as in Examples 1 to 33 provides a solvent-soluble fraction at a higher yield, as compared with the method of extracting a lignin degradation product from existing lignin as in Comparative Examples 7 and 8.

Further, it is known that, according to the method of separating lignin using a solvent capable of realizing two-phase separation as in Examples 15 to 26, a solvent-soluble fraction having a low softening point can be obtained, as compared with the method of extracting a lignin degradation solvent from a one-phase mixed solvent as in Comparative Examples 10 to 16.

Consequently, it may be said that the lignin production method of the present invention is especially useful in the point that, when a woody biomass or a plant biomass that contains a herbaceous biomass is used as the starting raw material, a high-quality lignin degradation product and a high-quality solvent-soluble fraction can be obtained at a high yield.

According to the production method for a lignin degradation product of the embodiment of the present invention, a lignin degradation product and a solvent-soluble fraction can be obtained efficiently, and the reason could be presumed as follows.

First, the fact that the recovered solid fraction could be mainly cellulose, and that one having dissolved in the organic phase could be mainly lignin are presupposed.

Examples 17, 23 and 26, and Comparative Examples 10, 12, 15 and 16 in Table 3 are compared. It is known that, according to the method of Examples, especially in the case where 1-butanol or 1-hexanol is used as the alcohol, the proportion of the lignin degradation product in the organic phase is high and the yield of the solvent-soluble fraction, based on lignin in the raw material, is high. In addition, since the cellulose content in the raw material bagasse is 45% by mass, it is considered that the value nearer to the content value means that the lignin content in the solid fraction is smaller.

It has been confirmed that lignin is more easily soluble in a mixed solvent of alcohol and water than in an organic solvent alone such as alcohol or the like. Lignin has a macromolecular structure, and contains many aromatic rings in the structure, and has a hydroxyl group therein. Consequently, it is considered that lignin would be hydrophilic/hydrophobic.

In addition, it is considered that, since lignin has hydrophobic mutual interaction between the aromatic rings therein and has intermolecular force such as hydrogen bonding between the hydroxyl groups therein, relatively low-molecular-weight molecules thereof could apparently form ultra-macromolecular molecules owing to the intermolecular mutual interaction.

Accordingly, it may be presumed that, for dissolving lignin, use of a solvent capable of cutting the intermolecular interaction of lignin would be effective. In other words, the solvent for dissolving lignin is desired to have a suitable balance of hydrophilicity and hydrophobicity. It is considered that a mixed solvent of water and alcohol could suitably satisfy the requirement.

It is said that pellets of a biomass raw material have cellulose in the center thereof, and hemicellulose covers the periphery of cellulose through hydrogen bonding, and lignin covers the outermost surface through ester or ether-bonding to hemicellulose.

It could hardly be considered that the intermolecular bond in lignin could be cut at a degradation reaction temperature of 200° C., and therefore at 200° C., it may be considered that hemicellulose would degrade and lignin would peel off while the intermolecular force thereof may be weakened by the mixed solvent of water and alcohol. At the degradation reaction temperature of 200° C., lignin that could hardly peel off from the raw material may be peeled off, for example, through bleaching treatment or the like.

As presumed to be like in the above, it is considered that, as the solvent for dissolving lignin, a mixed solvent of water and an organic solvent (alcohol) would be more suitable than an organic solvent alone.

In addition, for example, in a case where a one-phase mixed solvent with an alcohol having a lower boiling point than that of water is used, the alcohol alone may be evaporated away from the mixed solvent and lignin having dissolved in the alcohol may be thereby precipitated and recovered. However, for recovering a part of lignin having dissolved in water, more heat energy would be needed and therefore the heat energy loss is great and, in addition, it is difficult to increase the recovery of lignin. Further, in the case, the recovery of a component that contributes toward softening point depression would be insufficient and therefore it may be presumed that the softening point of the solvent-soluble fraction would rise. From these, it may be considered that, as the solvent for dissolving lignin, a mixed solvent of water and an organic solvent (alcohol) capable of realizing two-phase separation is suitable.

The difference in the yield between Examples where 1-butanol or 1-hexanol is used and Comparative Examples would result from the above-mentioned mixed solvent that is in one-phase state and from the type of the alcohol to form the mixed solvent. In addition, from the viewpoint of the ability to cut the intermolecular bond in lignin to secure the interaction with lignin, or that is, the balance of hydrophilicity/hydrophobicity thereof, it is considered that a mixed solvent of 1-butanol or 1-hexanol and water would be good.

The effect expressing mechanism of the present invention is not limited to the above-mentioned presumption.

The invention claimed is:

1. A method for producing a lignin degradation product, comprising:
   (1) a degradation step of degrading a raw material containing bagasse, in a mixed solvent of water and an aliphatic alcohol having from 4 to 10 carbon atoms, which separates into two phases at 0° C. or higher and 50° C. or lower, under the following conditions A to E;
   condition A: a concentration of the raw material in the mixed solvent is 1% by mass or more and 20% by mass or less,
   condition B: a reaction temperature is 100° C. or higher and 350° C. or lower,
   condition C: a reaction time is 1 hour or more and 3 hours or less,
   condition D: a pressure of the reaction system is from 0.5 MPa to 30 MPa, and
   condition E: the degradation step is carried out under an atmosphere where oxygen is reduced through nitrogen purging; and
   (2) after the degradation step, a liquid-liquid separation step of separating the lignin degradation product-containing organic phase from the mixed solvent that has separated at the temperature for two-phase separation,
   wherein the lignin degradation product has the following properties:
      (a) a weight-average molecular weight (Mw) of lignin degradation product in the lignin degradation product-containing organic phase is 1100 or more and 5000 or less, and
      (b) a softening point is 135° C. or lower.

2. The method for producing a lignin degradation product according to claim 1, wherein the concentration of the raw material in the mixed solvent under the condition A is 5% by mass or more and 20% by mass or less.

3. The method for producing a lignin degradation product according to claim 1, wherein the reaction temperature in the condition B is 150° C. or higher and 300° C. or lower.

4. The method for producing a lignin degradation product according to claim 1, wherein the aliphatic alcohol is at least one selected from 1-butanol, 1-pentanol and 1-hexanol.

* * * * *